United States Patent [19]

Margulies et al.

[11] 4,333,458
[45] Jun. 8, 1982

[54] SELF-ASPIRATING SYRINGE WITH POSITIVELY ENGAGED LOCKING COLLET

[75] Inventors: Herman Margulies, South Orange, N.J.; William G. Webb, East Greenbush, N.Y.

[73] Assignee: Sterling Drug Inc., New York, N.Y.

[21] Appl. No.: 232,634

[22] Filed: Feb. 9, 1981

[51] Int. Cl.³ ............................................ A61M 5/22
[52] U.S. Cl. .......................... 128/218 R; 128/218 D
[58] Field of Search ......... 128/218 R, 218 P, 218 PA, 128/218 D, 218 F, 215, 276, 234, 224

[56] References Cited

FOREIGN PATENT DOCUMENTS 1508686 11/1967 France .

Primary Examiner—John D. Yasko
Attorney, Agent, or Firm—William G. Webb; B. Woodrow Wyatt

[57] ABSTRACT

A hypodermic syringe of the automatic, or self-aspirating, type for use in combination with cartridge ampoules closed at one end by a diaphragm pierceable by a double-ended hypodermic needle and closed at the other end by a slidable piston consists of a syringe holder adapted to generate aspirating conditions within the cartridge ampoule by the slight backward displacement of the slidable piston by means of a double plunger, one slidable within, and biased against, the other, the inner plunger being positively interengaged with the slidable piston of the cartridge ampoule, and axial movement of the outer plunger being positively restricted by means for locking the other plunger with a collet in the end of the syringe holder.

7 Claims, 5 Drawing Figures

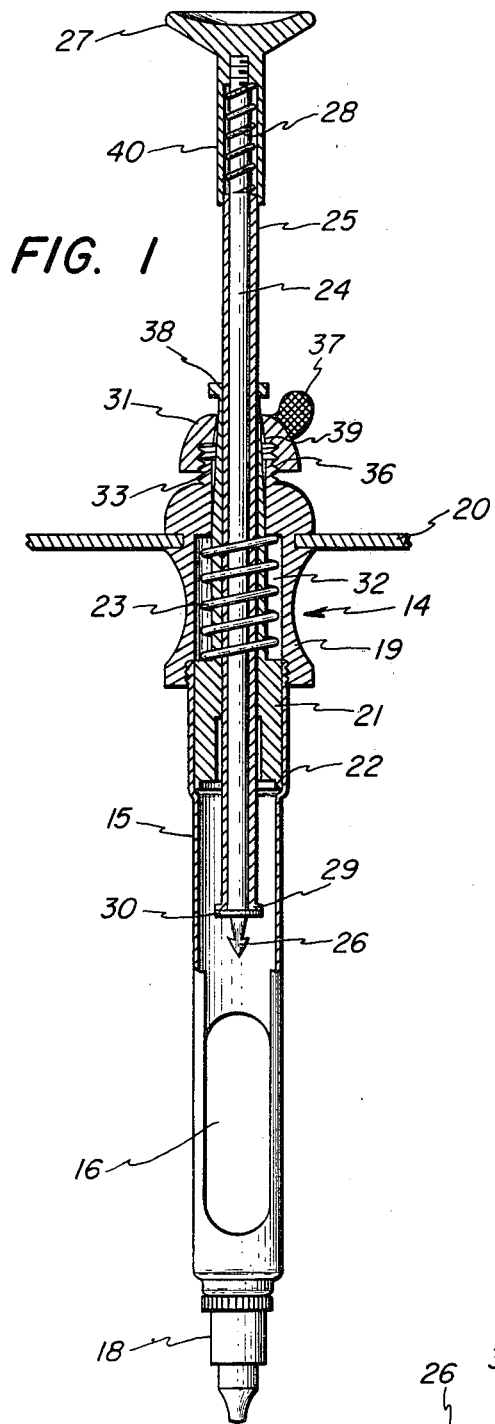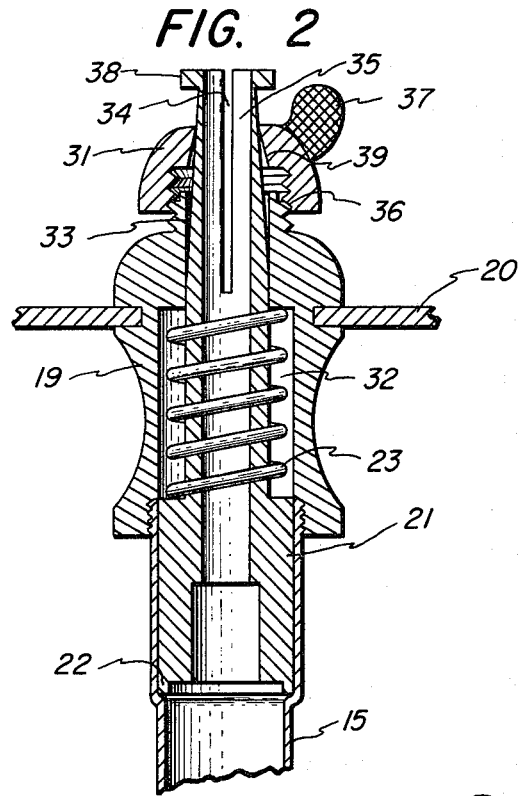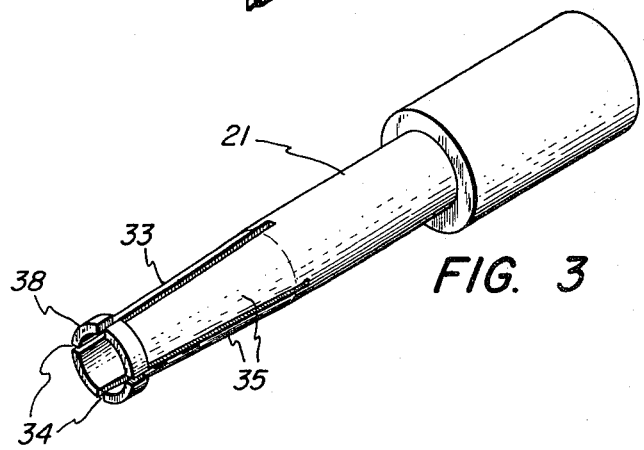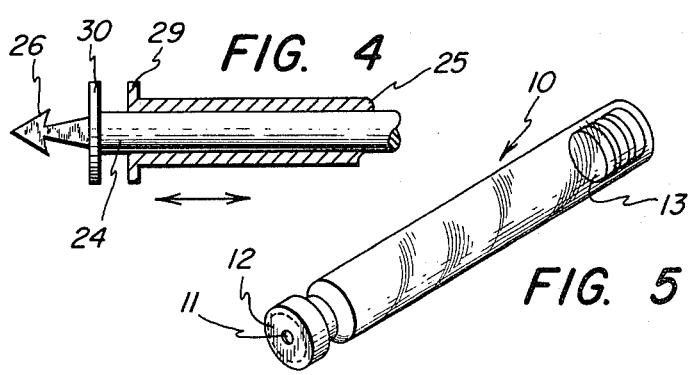

SELF-ASPIRATING SYRINGE WITH POSITIVELY ENGAGED LOCKING COLLET

BACKGROUND OF THE INVENTION

In medical practice, hypodermic injections are sometimes administered subcutaneously, while others must be given intravenously, depending upon the particular medication to be administered. In either case, it is essential that the practitioner know with certainty, prior to injection of the medication, whether the hypodermic needle tip is located in a major blood vessel, such as a vein, or in subcutaneous tissue. Use of an aspirating syringe in which a negative pressure can be generated in the syringe affords a means of making such determination. Thus the appearance of blood in the syringe upon generation of the negative pressure would indicate location of the needle tip in a major blood vessel, while the lack of appearance of blood would indicate location of the tip in subcutaneous tissue. Depending upon the type of injection intended, the injection can then either proceed directly, or if appropriate the tip can be withdrawn and relocated.

Aspirating syringes useful for the above stated purpose are generally of two types, that is either manually or automatically actuated. It is conventional in both manual as well as automatic aspirating syringes to use cartridge ampoules of the disposable, pre-loaded type, the lower end of which is closed by a flexible rubber diaphragm, which is pierceable by one end of a double-ended needle and secured to the ampoule by a crimped-on overcap, the upper end being closed by a piston slidable within the bore of the cartridge ampoule.

Syringes of the automatic aspirating type are often referred to as self-aspirating syringes. The syringes provided by the present invention are of the latter type and are used in conjunction with disposable cartridge ampoules of the type described above.

THE PRIOR ART

Aspiration in syringes of the manual type used with cartridge ampoules is usually effected by slightly withdrawing the syringe plunger rod after it has been connected to the slidable ampoule piston. Connection between the plunger rod and the slidable piston can be effected by a variety of means, such as by a screw-threaded engagement as in Schmidt, U.S. Pat. No. 3,797,487; by an interlocking jaw/coupling button as in Sarnoff, U.S. Pat. No. 3,115,135; or by a barb or "harpoon" on the syringe plunger which pierces and engages the rubber piston as in Jalar et al., U.S. Pat. No. 2,904,044 or Melott, U.S. Pat. No. 3,224,445. Alternatively, the body of the ampoule itself is withdrawn after locking a slidable ampoule piston to a central hollow post in the syringe body, for example by a screw-threaded engagement, as in Ogle, U.S. Pat. No. 3,739,780. Such manually actuatable aspirating syringes, however, have the disadvantage that their proper use depends in very large measure on the degree of skill of the person administering the injection.

Aspiration in syringes of the automatic or self-aspirating type is effected by first inducing a positive pressure in a medicament-containing portion of the syringe, for example in a disposable cartridge ampoule. On release of the force inducing the positive pressure, a corresponding negative pressure in the syringe is generated thus giving rise to the aspirating effect. In Ritsky, U.S. Pat. No. 3,583,399, induction of the positive pressure is achieved by the inward flexing of a rubber diaphragm, which closes the lower end of a medicament-containing ampoule and which is pierceable by the inner end of a double-ended needle, such flexing resulting from impingement of the lower end of the ampoule against a fixed stud surrounding the inner end of the double-ended needle when the ampoule is pressed downwards. Release of the pressure against the ampoule causes return of the diaphragm to its original planar configuration and consequent generation of a slight negative pressure in the ampoule. Self-aspirating syringes of the type described by Ritsky however have the disadvantage that the self-aspirating effect depends greatly on the elasticity of the rubber diaphragm, and the elasticity in turn depends on a number of other variables such as the type, quality and thickness of the rubber and the size of the opening in the end of the ampoule over which the rubber diaphragm is stretched. Thus, syringes equipped with the stud-actuated self-aspirating feature require the use of carefully standardized ampoules.

In Evers et al., U.S. Pat. No. 3,295,525 and Cox, U.S. Pat. No. 3,340,872, induction of the positive pressure in the medicament-containing ampoule is achieved by the action of a flexible portion of the slidable rubber piston which closes the upper end of the ampoule. In these devices, downward pressure on the syringe plunger causes inward distention of the flexible portion of the rubber piston thus producing the desired positive pressure in the ampoule. Release of pressure against the plunger results in return of the flexible portion to its undistended condition and consequent generation of a slight negative pressure in the ampoule. Self-aspirating syringes of the type described by Evers et al. and Cox suffer from the disadvantage that the rubber pistons, with the flexible portions as an integral part thereof, require special molding and are thus more expensive than conventional rubber pistons.

A rather elaborate method of achieving self-aspiration in a hypodermic syringe unit is that shown by Black U.S. Pat. No. 3,433,223 which describes a gas powered injection system in which self-aspiration is generated by holding the piston of a cartridge ampoule stationary while the ampoule is moved forward, thus in effect producing a backward motion of the piston.

BRIEF SUMMARY OF THE INVENTION

Ideally a self-aspirating hypodermic syringe employing disposable cartridge ampoules should be relatively simple in construction so as to minimize the cost of production; should be relatively simple to operate; should be capable of manipulation with one hand; should be adaptable to multiple self-aspirating actions with each ampoule; should be capable of expelling trapped air from the ampoule prior to insertion of the needle into the injection site and prior to initiation of the self-aspirating action without either precluding self-aspirating action at a later time in the operation sequence of the syringe or otherwise rendering it inoperative; and should be so-constructed that the self-aspirating hypodermic syringe, either in whole or in part, can be marketed either as single-use disposable (i.e. plastic) units or as reusable units marketed as a self-aspirating hypodermic syringe unit for use in combination with the cartridge ampoules.

The self-aspirating syringe provided by the present invention mimics, automatically, the slight rearward piston displacement action of manually operable syringes, thus generating the slight negative pressure in the cartridge ampoule essential for aspiration. The syringe of the present invention therefore obviates the disadvantages inherent in prior art syringes of either the manual type, since the aspirating action is generated automatically which requires no special skill on the part of the practitioner. It also obviates the disadvantages of syringes of the automatic (i.e. self-aspirating) type, because aspirating action is achieved independently of the elasticity of the rubber diaphragm of the cartridge ampoule, and it furthermore utilizes cartridge ampoules with standard rubber pistons. The syringe provided by the invention moreover achieves each of the above-indicated objectives of an ideal self-aspirating syringe.

More specifically the present invention is directed to a hypodermic syringe holder adapted to securely hold within the barrel thereof a medicament-containing cartridge ampoule, the syringe holder being equipped with a pair of plungers, one slidable within the other, said plungers being biased one against the other, the inner plunger being adapted for positive interengagement with the slidable piston of the cartridge ampoule, and the syringe holder being provided with means for positively locking the outer plunger against axial movement relative to the barrel of the syringe holder by means of a collet located in the head of the syringe holder, the inner and outer plungers being slidable within the collet, whereby upon alternate exertion of downward pressure upon the inner plunger and release thereof when the outer plunger is locked by the collet, the bias of one plunger against the other produces slight withdrawal of the slidable piston in the cartridge ampoule thereby generating aspirating conditions in the same, and whereby the inner and outer plunger are freely slidable within the collet when the outer plunger is unlocked.

BRIEF DESCRIPTION OF THE DRAWINGS

The invention is described hereinbelow with reference to the accompanying drawings wherein:

FIG. 1 is a view in partial longitudinal section of a self-aspirating syringe of the invention;

FIG. 2 is a view in enlarged longitudinal section of the head portion of the self-aspirating syringe of the invention;

FIG. 3 is a perspective view of the collet/locking sleeve used with the syringe of FIG. 1;

FIG. 4 is an elevational view in partial longitudinal section of the inner end of the double plunger used with the syringe of FIG. 1 illustrating the plunger mechanism in an aspirating mode; and FIG. 5 is a perspective view of a cartridge ampoule used with the syringe of FIG. 1.

DETAILED DESCRIPTION OF THE INVENTION

The invention will now be described in detail with reference to the foregoing figures where like numerals are used to designate like parts.

In the foregoing discussion and elsewhere in the specification and appended claims, the terms "lower" and "downward" are intended to make reference to the needle end of the hypodermic syringes and associated parts described herein, and conversely the terms "upper" and "upward" are intended to make reference to the head end thereof.

FIG. 5 illustrates a cartridge ampoule, generally indicated by reference numeral 10, of a well-known type which consists of a cylindrical container, usually glass or clear plastic, having a necked-down end and sealed at the necked-down end with a rubber diaphragm 11 which is secured to the ampoule by a crimped-on metal collar 12. The other end of the ampoule is closed by a piston 13 which is slidable in the bore of the ampoule.

The self-aspirating concept of the present invention is used in conjunction with syringe holders of the side loading type. One such embodiment, generally indicated by the reference numeral 14, is illustrated in FIG. 1 with details thereof shown in FIGS. 2 and 3. The syringe there depicted has a hollow tubular body or barrel 15 having an elongated window 16 therein for insertion of a cartridge ampoule 10, only the lower end of window 16 being depicted in the partial section view of FIG. 1. The syringe holder is fitted at its lower end with a needle hub 18 which is either detachably or integrally fitted with a hypodermic needle (not shown), the needle hub unit itself being detachably fitted to the syringe holder, for example by means of a screw-threaded mounting. The needle is of the double-ended type so that when a cartridge ampoule 10 is inserted in the syringe barrel 15, the inner end of the needle pierces the diaphragm 11 so that the needle is in communication with the contents of the ampoule. The barrel 15 is attached to, and extends from, a head unit 19 to which is attached a pair of finger grips 20.

In the practice of the present invention, it is necessary that the ampoule 10 be essentially immobilized within the barrel 15 of the syringe holder, and accordingly for this purpose the head 19 is equipped with a locking sleeve 21 of generally cylindrical configuration, the shoulder 22 of which is biased downwards against the rim of the cartridge ampoule by compression spring 23. Slidably mounted within the bore of the locking sleeve is a double plunger which is composed of an inner plunger rod 24 which itself is slidable within the bore of a sleeve or outer plunger 25. The inner plunger rod is fitted at its lower end with any conventional means for making positive interengagement with the rubber piston 13 in the cartridge ampoule 10. For purposes of illustration, this interengagement means is depicted herein as a barbed point or "harpoon" 26 which is well known in the art for the stated purpose. However, it is to be understood that other conventional means of effecting interengagement between the plunger and the piston, such as those described in the PRIOR ART section above, will serve the purpose as well. The upper end of the inner plunger is fitted with a thumb plate 27 with a skirt 40 depending therefrom, and the inner plunger and outer plunger or sleeve are biased one against the other by a coil spring 28.

The lower end of the outer plunger or sleeve is fitted with an annular rim 29 which serves to prevent removal of the inner/outer plunger assembly from the bore of the locking sleeve 21. The lower end of the inner plunger rod is also fitted with an annular rim 30 which serves to prevent removal of the inner plunger from within the bore of the sleeve or outer plunger. The thumb plate and skirt unit are threadably engaged with the upper end of the inner plunger. The threaded interengagement of the thumb plate and skirt unit with the plunger provides a means for assembling the inner/outer plunger unit within the head of the syringe. This assembly is accomplished by first removing the thumb plate/skirt/coil spring units 27/40/28 from the outer plunger, passing the inner and outer plungers, one within the other, through window 16 and upward through the bore of locking sleeve 21 and reassembling the coil spring and thumb plate/skirt units to the inner plunger.

The locking sleeve 21, at its widest diameter, is slidable within the bore of the syringe head 19, and at its upper end has a section of diminished diameter which is slidable through the end opening of the syringe head and the opening through a locking nut 31 to be described hereinbelow. The upper end of the locking sleeve passes through a cavity 32 in the head of the syringe which is of sufficient diameter to accommodate a compression spring 23 which, as pointed out above, serves to bias the shoulder 22 of the locking sleeve 21 downwards against the rim of ampoule 10.

The upper end of the locking sleeve 21 having the smaller diameter is tapered as at 33 in FIG. 2 and FIG. 3 and is furthermore provided with slots 34 which form an equal number of flexible fingers 35.

The locking nut 31 mentioned above is fitted to the head of the syringe by means of threaded engagement 36. The pitch of the threads is preferably selected so that the locking nut can be turned from its full up to its full down position in about one quarter turn of the nut. The locking nut is fitted with a thumb tab 37 to permit positive, selective and reversible manipulation of the locking nut by the operator as will be more fully described below, and the locking nut is prevented from being fully removed from the syringe head by an annular retaining flange 38 on the ends of the fingers 35. The interior wall of the locking nut has a sloping surface 39 which is so configured that it generally conforms to the tapered surface 33 of locking sleeve 21. Thus with the locking nut in the full up or open position, the flexible fingers 35 are uncompressed, and the inner/outer plunger assembly 24/25 is freely slidable in the bore of the locking sleeve. However when the locking nut is turned to its full down or closed position, the sloping surface 39 of the locking nut slides downward over the mating tapered surface of the locking sleeve forcing the fingers inward against the outer plunger 25 thereby locking it against axial movement relative to the syringe holder. Thus it is seen that the locking sleeve 21 serves a dual purpose as a locking sleeve to immobilize the cartridge ampoule in the syringe barrel and as a collet to positively, selectively and reversibly lock the outer plunger against axial movement.

In use the syringe of FIG. 1 is first loaded with a cartridge ampoule 10 by withdrawing the plunger/locking sleeve against the bias of compression spring 23, inserting the ampoule through window 16, and releasing the plunger/locking sleeve. Engagement between the inner plunger rod 24 and the piston 13 is made, and in syringes having a detachable needle and needle hub unit, such unit is then attached. After air is expelled from the cartridge by downward pressure on thumb plate 27, the needle is inserted in the injection site. When the operator wishes to aspirate to determine whether the needle tip has pierced a vein, he turns the locking nut 31 to its full down position by applying thumb pressure against thumb tab 37 thus securely locking the fingers 35 of the collet/locking sleeve 21 against the surface of outer plunger 25 and immobilizing the same against axial movement. Thereafter when further downward pressure is exerted on thumb plate 27, the inner plunger 24 advances beyond the outer plunger 25 as shown in FIG. 4. When pressure on the thumb plate is released, the inner plunger is withdrawn by the force generated by coil spring 28, and the inner and outer plungers will once again assume the relative positions with respect to one another indicated in FIG. 1. As the inner plunger is withdrawn, the piston 13 to which it is firmly engaged via interengagement means 26 is likewise withdrawn slightly thus generating a slight negative pressure in the ampoule and creating aspirating conditions within the same. When the locking nut 31 is returned to its full up or open position by reverse manipulation of the thumb tab 37, the collet is unlocked, and injection can thus be made by continued downward pressure on thumb plate 27.

It will be appreciated from the foregoing description that the self-aspirating syringe provided by the present invention possesses all the attributes of an ideal aspirating syringe as enumerated above. That is the syringe is relatively simple in construction, thus minimizing the cost of production; it is relatively simple to operate; it is capable of manipulation with one hand; it is capable of multiple self-aspirating actions with each cartridge ampoule; and it is capable of expelling trapped air from the ampoule either prior to initiation of the self-aspirating action or at any time during the sequence of actions necessary for injection of the ampoule contents without, on the one hand, precluding self-aspirating action at any point in the sequence or, on the other, rendering the self-aspirating action inoperative.

Moreover, the self-aspirating syringe of the invention can be constructed either in whole or in part from metal, to provide reusable units, or from plastic, to provide disposable units.

It will also be understood that, although the preferred embodiments of the invention have been described above in order to better illustrate the same, alternative structural features can be substituted for elements described herein without either departing from the spirit of the invention or in any way adversely affecting the operability of the same. For example, as mentioned above, alternative conventional means of achieving interengagement between the inner plunger and the slidable ampoule piston can be used. Furthermore, a thumb ring conventionally used in manually operating aspirating syringes, although not essential in the operation of the present automatic self-aspirating system, can nevertheless be used in place of a thumb plate.

Having thus described the invention and the advantages thereof, it is considered that the invention is to be broadly construed and limited only by the character of the following claims.

We claim:

1. A self-aspirating hypodermic syringe of the type used in combination with a cartridge ampoule which is sealed at its upper end by a slidable piston and at its lower end by a pierceable membrane, and which contains an injectable fluid therein, which comprises a syringe holder having:
   (A) a head;
   (B) a barrel attached thereto for receiving said cartridge ampoule and provided at its lower end with a double ended needle for communication with the cartridge ampoule contents; and
   (C) a generally cylindrical holding means within said head, said holding means being adapted for:
   (1) securely holding said cartridge ampoule within said barrel;
   (2) receiving within the bore thereof a double plunger mechanism comprising an inner plunger slidable within the bore of, and biased against, an outer plunger, said inner plunger having interengagement means for making positive interengagement with the slidable piston closing the upper end of said cartridge ampoule; and (3) positively, selectively and reversibly locking said outer plunger within the head of said syringe holder thereby to immobilize said outer plunger against axial movement relative to said syringe holder, whereby upon alternate exertion of downward pressure upon said inner plunger and release thereof when said holding means is in locking engagement, the bias of said inner plunger against said outer plunger creates aspirating conditions within said ampoule and whereby upon exertion of downward pressure upon said inner plunger when said holding means is unlocked, said inner and outer plungers are freely slidable within the bore of said holding means.

2. The self-aspirating hypodermic syringe according to claim 1 wherein said holding means comprises a spring-biased locking sleeve for engagement of the rim of said ampoule, the upper end of which is slotted to form flexible fingers to thereby function as a collet.

3. The self-aspirating hypodermic syringe according to claim 2 wherein the head of the syringe holder is provided with a screw-threaded locking nut, the interior wall of which impinges upon said flexible fingers to reversibly open and close the same.

4. The self-aspirating hypodermic syringe according to claim 3 wherein said flexible fingers are provided with a retaining flange to prevent removal of said locking nut from the head of said syringe.

5. The self-aspirating hypodermic syringe according to claim 4 wherein the locking nut is fitted with a thumb tab.

6. The self-aspirating hypodermic syringe according to claim 5 wherein the pitch of said screw-threaded locking nut is selected so as to move said locking nut from a full open to a full closed position by approximately one-quarter turn of said locking nut.

7. The self-aspirating hypodermic syringe according to claim 6 adapted for threadable attachment of a needle and needle hub unit.

* * * * *